US00PP21213P2

(12) United States Plant Patent
Brouwer

(10) Patent No.: US PP21,213 P2
(45) Date of Patent: Aug. 17, 2010

(54) ***SPATHIPHYLLUM* PLANT NAMED 'MICKEY'**

(50) Latin Name: ***Spathiphyllum* hybrid**
Varietal Denomination: MICKEY

(76) Inventor: Wim Brouwer, Nieuwkoopseweg 47, Nootdorp 2631 PP (NL)

( * ) Notice: Subject to any disclaimer, the term of this patent is extended or adjusted under 35 U.S.C. 154(b) by 0 days.

(21) Appl. No.: 12/380,501

(22) Filed: Feb. 27, 2009

(51) Int. Cl.
*A01H 5/00* (2006.01)

(52) U.S. Cl. ..... Plt./364

(58) Field of Classification Search ..... Plt./364
See application file for complete search history.

*Primary Examiner*—Susan B McCormick Ewoldt

(57) ABSTRACT

A new and distinct *Spathiphyllum* cultivar named 'MICKEY' is disclosed, characterized by prolific spathe production, very compact plant growth, and bright white and white/green spathe color, without cream coloration. The new variety is commercially suitable for indoor plant production.

1 Drawing Sheet

Figure 1:
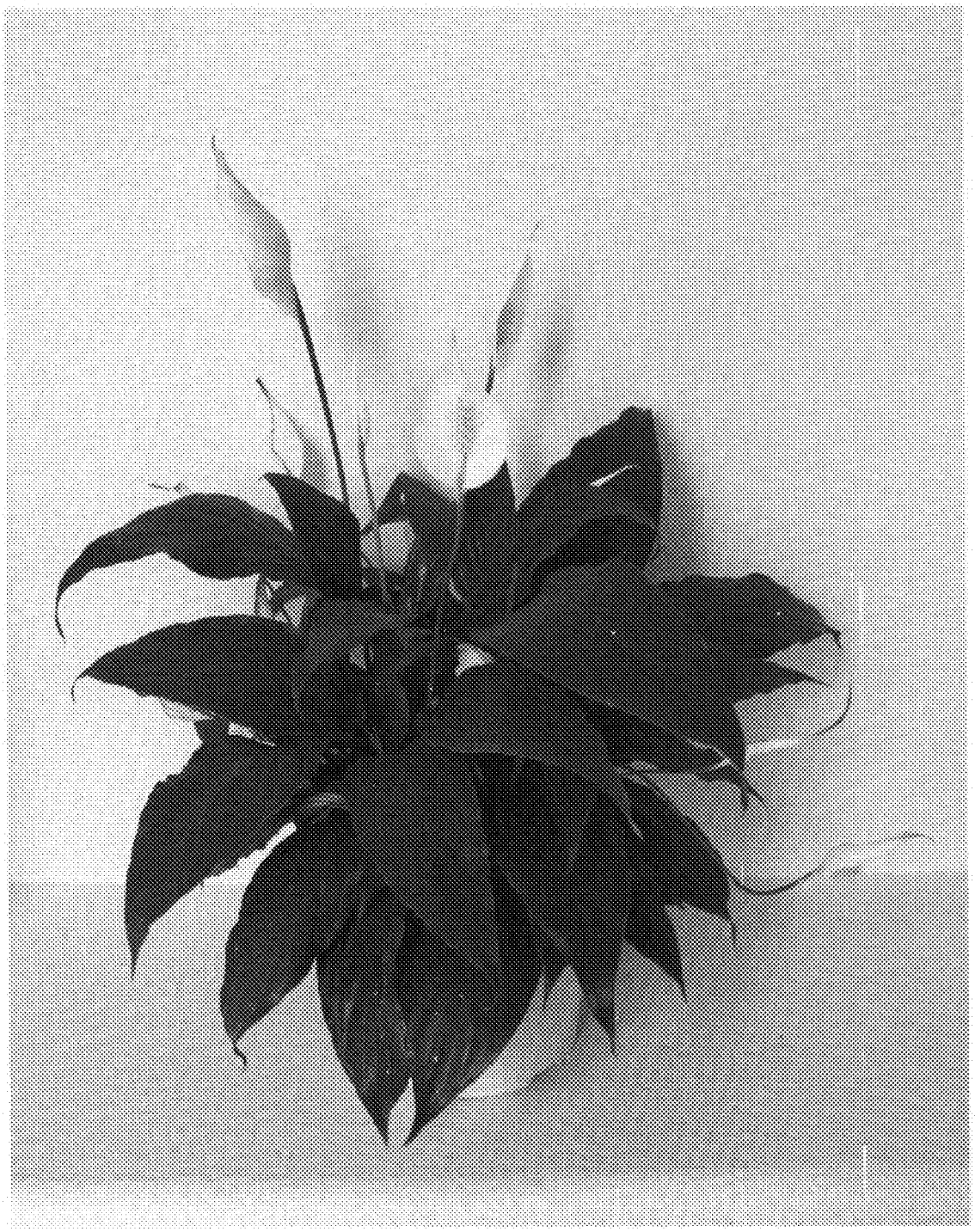

Latin name of the genus and species: *Spathiphyllum* hybrid.

Variety denomination: 'MICKEY'.

BACKGROUND OF THE INVENTION

The new cultivar is a product of a planned breeding program. The new variety originated from a cross pollination, made by the inventor in September 2004, of a proprietary seed parent identified as *Spathiphyllum* hybrid '286' and the pollen parent *Spathiphyllum* hybrid 'Carlos,' U.S. Plant Pat. No. 15,476.

The new variety was discovered by the inventor, Wim Brouwer, a citizen of the Netherlands, in December 2005 in a group of seedlings resulting from the crossing. The new cultivar was found in a commercial green house belonging to the inventor in Nootdorp, the Netherlands.

Asexual reproduction of the new cultivar 'MICKEY' was first performed at a commercial laboratory in the Netherlands by tissue culture in January 2006. 'MICKEY' has been reproduced by micro-propagation and has shown that the unique features of this cultivar are stable and reproduced true to type.

SUMMARY OF THE INVENTION

The cultivar 'MICKEY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MICKEY.' These characteristics in combination distinguish 'MICKEY' as a new and distinct *Spathiphyllum* cultivar:

1. Prolific spathe production.
2. Very compact plant.
3. Bright white and white/green spathe color, without cream coloration.

PARENT COMPARISON

Plants of the new cultivar 'Mickey' are similar to plants of the seed parent variety, '286' in most horticultural characteristics, however, plants of the new cultivar produce a smaller overall plant and smaller spathes than the seed parent.

Plants of the new cultivar 'Mickey' are similar to plants of the pollen parent variety, 'Carlos' in most horticultural characteristics, however, plants of the new cultivar produce a smaller overall plant, brighter white spathes, and more spathes per plant.

COMMERCIAL COMPARISON

Plants of the new cultivar 'Mickey' are similar to plants of the patented variety, *Spathiphyllum* hybrid 'Junior,' U.S. Plant Pat. No. 15,713 in most horticultural characteristics, however, plants of the new cultivar produce more spathes per plant, and take approximately 3 weeks longer to begin flowering.

BRIEF DESCRIPTION OF THE PHOTOGRAPH

The accompanying photograph in FIG. 1 illustrates in full color a typical plant of 'MICKEY' grown in a greenhouse in Apopka, Fla. This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'MICKEY' plants grown in a climate controlled greenhouse in Apopka, Fla., USA. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Spathiphyllum* hybrid cultivar 'MICKEY.'

PROPAGATION

Time to initiate roots: Approximately 8 days from an initial cutting at approximately 20 to 22° C.
Time to produce rooted plantlet: Approximately 7 weeks at approximately 20 to 22° C.
Root description: Fine, fibrous.

PLANT

Growth habit: Leaves growing directly from base of plant, forming a round plant shape.
Plant shape: Upright, leaves slightly arching out.
Height: Approximately 25 cm to top of highest leaf, approximately 36 cm to top of highest spathe.
Plant spread: Approximately 40 cm in a 6 inch pot.
Normal pot size: 4 and 6 inch and larger.
Growth rate: Moderate.
Branching characteristics: No branching. Leaves emerge direct from base of plant.
Number of clumps of leaves: 10.
Number of leaves per clump: Average 15.
Number of leaves per plant: Approximately 150.
Age of plant described: Approximately 9 months.

FOLIAGE

Leaf:
*Arrangement.*—Single leaves emerging basally.
*Average length(excluding petiole).*—Approximately 21 cm.
*Average width.*—Approximately 7.5 cm.
*Shape of blade.*—Elliptic.
*Aspect.*—Slightly recurved.
*Apex.*—Apiculate.
*Base.*—Attenuate.
*Margin.*—Entire.
*Texture of top surface.*—Smooth, moderately glossy.
*Texture of bottom surface.*—Smooth, moderately glossy.
*Color.*—Young foliage upper side: Near R.H.S. Green143A. Young foliage under side: Near R.H.S. Green 138B. Mature foliage upper side: Near R.H.S. Green139A. Mature foliage under side: Near R.H.S. Green139B.
Venation:
*Type.*—Pinnate.
*Venation coloration upper side.*—Green 139B.
*Venation coloration under side.*—Green 138A.
Petiole(excluding geniculum):
*Length.*—Approximately 8 cm.
*Width.*—At geniculum: Approximately 0.7 cm. Above clump: Approximately 1.3 cm.
*Color.*—Near RHS Green 138B
*Strength.*—Very strong.
Geniculum:
*Length.*—Approximately 6.5 cm.
*Width.*—Approximately 0.7 cm.
*Color.*—Near RHS Green 138B.
*Other characteristics.*—Tightly held to petiole.

INFLORESCENCE

Arrangement: Spathes with spadices held above the foliage on erect peduncles arising from the petiole sheath.
Flowering habit: Continuous.
Quantity of spathes per plant: On average 12 fully open spathes in good condition.
Natural flowering season: Autumn to Winter.
Time to flowering: 6 months.
Fragrance: Not present.
Self-cleaning or persistent: Persistent.
Flower longevity: Flowers stay in good condition approximately 6 weeks on the plant.
Spathe:
*Aspect.*—Slightly concave. More concave at base, mostly flat moving towards apex.
*Length: Approximately* 9.5 cm.
*Width: Approximately* 4.1 cm.
*Shape.*—Elliptic.
*Margin.*—Entire.
*Apex.*—Apiculate, with a slight twist occurring with age.
*Base.*—Cuneate.
*Color.*—Front when opening: Near RHS White 155C. Lateral veins of RHS Green 143B. Margin very faint Green 143C. Back when opening: Near RHS White 155C. Strong mid-vein and lateral veins of RHS Green 143C. Front when mature: Near RHS Green-White 157C. Lateral veins of RHS Green 143B. Margin very faint Green 143C. Back when mature: Near RHS Green-White 157C. Lateral veins of RHS Green 143B. Margin very faint Green 143C. Fading to: No fading.
Spadix:
*Shape.*—Columnar, arising from the top of the peduncle.
*Tip.*—Obtuse.
*Base.*—Obtuse.
*Length.*—Approximately 2.8 cm.
*Width.*—Approximately 1.2 cm.
*Color.*—When opening: Near RHS White 155A. Mature: Near RHS Yellow-Green 145D.
*Quantity of flowers per spadix.*—Approximately 50.
*Spadix flower arrangement.*—Bisexual, rounded.
*Spadix flower diameter.*—Approximately 0.2 cm.
*Spadix flower depth.*—Approximately 0.1 cm.
Peduncle:
*Length.*—Approximately 20 cm.
*Width.*—Approximately 0.4 cm.
*Color.*—Near RHS Green 138A.
*Strength.*—Moderate.

REPRODUCTIVE ORGANS

All parts are highly compact and indistinguishable. Pollen not observed.

OTHER CHARACTERISTICS

Disease resistance: Neither resistance nor susceptibility to diseases or pests has been observed in this variety.
Drought tolerance and cold tolerance: The new cultivar is a typical *Spathiphyllum*, cold tolerant to approximately 5 to 7C and does not tolerate drought.
Fruit/seed production: Not observed.

What is claimed is:

1. A new and distinct cultivar of *Spathiphyllum* plant named 'MICKEY' as herein illustrated and described.

* * * * *